United States Patent [19]

Inoue et al.

[11] Patent Number: 5,047,555

[45] Date of Patent: Sep. 10, 1991

[54] 4-AMINOPHENOL DERIVATIVES AND PROCESSES FOR PREPARING THE SAME

[75] Inventors: Hirozumi Inoue, Tokyo; Kei Tsuzurahara, Omiya; Katsuo Ikezawa, Urawa; Tomofumi Uchida, Habikino, all of Japan

[73] Assignee: Tanabe Seiyaku Co., Ltd., Osaka, Japan

[21] Appl. No.: 445,059

[22] Filed: Dec. 4, 1989

[30] Foreign Application Priority Data

Dec. 13, 1988 [JP] Japan .................................. 63-314792
Dec. 26, 1988 [JP] Japan .................................. 63-330643
Dec. 26, 1988 [JP] Japan .................................. 63-330644

[51] Int. Cl.$^5$ .................. C07D 207/33; C07D 333/38; C07D 235/38
[52] U.S. Cl. ..................................... 548/537; 549/49; 549/72; 548/494; 564/207
[58] Field of Search ..................... 564/207; 549/49, 72; 548/494, 537

[56] References Cited

U.S. PATENT DOCUMENTS

| | | | |
|---|---|---|---|
| 4,152,319 | 5/1979 | Kline | 260/45.9 NC |
| 4,222,946 | 9/1980 | Evans et al. | 260/347.3 |
| 4,677,113 | 6/1987 | Bell et al. | 514/448 |
| 4,731,376 | 3/1988 | Hideg et al. | 514/423 |

FOREIGN PATENT DOCUMENTS

| | | |
|---|---|---|
| 0776720 | 1/1968 | Canada .................. 260/560 |
| 0200443 | 11/1986 | European Pat. Off. . |
| 0286364 | 10/1988 | European Pat. Off. . |
| 0374084 | 6/1990 | European Pat. Off. . |
| 4624782 | 7/1971 | Japan . |
| 271268 | 12/1986 | Japan . |
| 62-53980 | 3/1987 | Japan . |
| 62-67023 | 3/1987 | Japan . |

OTHER PUBLICATIONS

Patent Abstracts of Japan, vol. 11, No. 133 (C-418)(2580), Apr. 25, 1987; & JP-A-61 271 268 (Hisamitsu Pharmaceut. Co. Inc.) Dec. 1, 1986 (Cat. D).
Patent Abstracts of Japan, vol. 11, No. 267 (C-443)(2714), Aug. 28, 1987; & JP-A-62 67 023 (Otsuka Pharmaceut. Factory Inc.) Mar. 26, 1987 (Cat. D).
Chemical Abstracts, vol. 77, No. 22, Jul. 10, 1972, p. 59, abstract No. 6555w, Columbus, Ohio, U.S.A.; & JP-71 24 784 (Cat. D).

Primary Examiner—Jose G. Dees
Assistant Examiner—Porfirio Nazario
Attorney, Agent, or Firm—Browdy and Neimark

[57] ABSTRACT

There are disclosed a 4-aminophenol derivative of the formula:

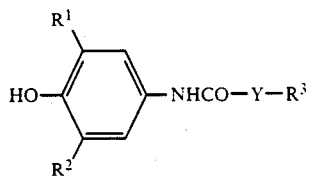

(wherein $R^1$ and $R^2$ each represent a lower alkyl group, Y represents a single bonding arm, a lower alkylene group or a lower alkenylene group, $R^3$ represents a thienyl group or pyrrolyl group which may be also substituted with a lower alkyl group; benzothienyl group, indolyl group; or a phenol group which is substituted with 1 to 2 groups selected from a lower alkoxy group and a lower alkanoyloxy group; or Y-$R^3$ represents integrally an alkyl group with 6 to 9 carbon atoms; or a hydrocarbon group with 5 to 14 carbon atoms having 2 or 3 double bonds) or a pharmacologically acceptable salt thereof, and processes for preparing the same.

11 Claims, No Drawings

4-AMINOPHENOL DERIVATIVES AND PROCESSES FOR PREPARING THE SAME

This invention relates to a novel 4-aminophenol derivative or a salt thereof which is useful as lipoxygenase inhibitor.

In the prior art, as the compound having lipoxygenase inhibitory activity, for example, 4-[2-(5-methyl)-thiazolylamino]-2,3-di-tert-butylphenol (Japanese Provisional Patent Publication No. 67023/1987) and 2-ethoxycarbonyl or 2-benzyloxycarbonyl derivative of 3-methyl-4-hydroxy-5-n-propyl-7-fluorobenzofuran (Japanese Provisional Patent Publication No. 53980/1987), etc. have been known Also, these compounds are reported to be useful for therapy or prophylaxis of allergic diseases such as asthma, etc.

Also, 2,6-dichloro-4-aminophenol derivatives, for example, 2,6-dichloro-4-(3,4,5-trimethoxybenzoyl)aminophenol are known to have immune control activity or PCA (passive cutaneous anaphylaxis) inhibitory activity (Japanese Provisional Patent Publication No. 271268/1986). Further, 4-(lauroylamino)-2-ethyl-6-tert-butylphenol, 4-(stearoylamino)-2,6-di-tert-butylphenol are known to have antioxidant activity and be useful as stabilizer for polymers (Japanese Patent Publication No. 24782/1971).

SUMMARY OF THE INVENTION

The present invention concerns a novel 4-aminophenol derivative represented by the formula shown below or a salt thereof:

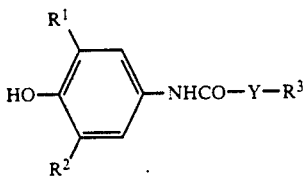

(wherein $R^1$ and $R^2$ each represent a lower alkyl group,
(A) Y represents a single bonding arm, a lower alkylene group or a lower alkenylene group, and
$R^3$ represents (1) a thienyl group or pyrrolyl group which may be substituted with a lower alkyl group;
(2) benzothienyl group or indolyl group, or
(3) a phenyl group which is substituted with 1 to 2 groups selected from a lower alkoxy group and a lower alkanoyloxy group, or
(B) Y-$R^3$ represents (4) integrally an alkyl group with 6 to 9 carbon atoms or (5) a hydrocarbon group with 5 to 14 carbon atoms having 2 or 3 double bonds).

DESCRIPTION OF THE PREFERRED EMBODIMENTS

The desired product (I) of the present invention and its salt have excellent lipoxygenase inhibitory activity, and are useful pharmaceutical compounds as antiallergics and antiinflammatory agents. Preferred examples of the desired product of the present invention may include those of the formula (I), wherein Y is a single bonding arm, a lower alkylene group or a lower alkenylene group, and $R^3$ is a thienyl group or pyrrolyl group which may be also substituted with a lower alkyl group, a benzothienyl group or an indolyl group. Among them, those wherein $R^3$ represents thienyl group, a 2-(lower alkyl)thienyl group, pyrrolyl group, an N-(lower alkyl)-pyrrolyl group, benzothienyl group or indolyl group may be more preferred. Other preferred examples of the desired product of the present invention may include those of the formula (I), wherein Y is a single bonding arm, a lower alkylene group or a lower alkenylene group, and $R^3$ is a phenyl group substituted with 1 to 2 groups selected from a lower alkoxy group and a lower alkanoyloxy group. Among them, those wherein $R^3$ represents a 3-or 4-(lower alkoxy)phenyl group, a 3,4-di(lower alkoxy)-phenyl group, a 2,5-di(lower alkoxy)-phenyl group or a 3,4-di(lower alkanoyloxy)phenyl group may be more preferred. Still other preferred examples of the desired product of the present invention may include those of the formula (I), wherein Y-$R^3$ represents integrally an alkyl group with 6 to 9 carbon atoms or a hydrocarbon group with 5 to 14 carbon atoms having 2 or 3 double bonds.

In the present invention, examples of the lower alkyl group, the lower alkoxy group, the lower alkanoyloxy group, the lower alkylene group and the lower alkenylene group may include respectively alkyl groups with 1 to 4 carbon atoms, alkoxy groups with 1 to 4 carbon atoms, alkanoyloxy groups with 2 to 5 carbon atoms, alkylene groups with 1 to 4 carbon atoms and alkenylene groups with 2 to 4 carbon atoms As the salt of the desired product (I), for example, basic salts such as alkali metal salts (e.g. sodium salt, potassium salt, etc.), alkaline earth metal salt (e.g. calcium salt, etc.), aluminum salts may be included. When $R^3$ is pyrrolyl group which may be substituted with a lower alkyl group, the desired product (I) can be also made an inorganic acid addition salt such as hydrochloride, hydrobromide and sulfate; an organic acid addition salt such as acetate, oxalate and benzenesulfonate.

According to the present invention, the desired product (I) can be prepared by subjecting an aniline compound of the formula:

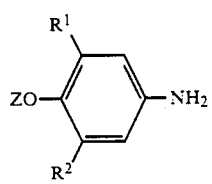

(wherein ZO represents a hydroxyl group or a protected hydroxyl group, and $R^1$ and $R^2$ have the same meanings as defined above) or a salt thereof and a carboxylic acid compound of the formula:

$$HOOC-Y-R^3 \quad (III)$$

(wherein $R^3$ and Y have the same meanings as defined above),
or a reactive derivative or a salt thereof to condensation reaction, and when ZO is a protected hydroxyl group, eliminating the protective group from the product.

Also, of the desired compounds (I), the compounds of the formula:

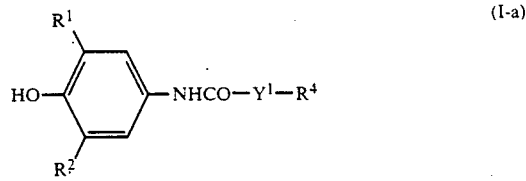

(wherein $R^1$ and $R^2$ have the same meanings as defined above, $Y^1$ represents a lower alkylene group with 2 or more carbom atoms, and $R^4$ represents a thienyl group or pyrrolyl group which may be also substituted with a lower alkyl group; benzothienyl group, indolyl group; or a phenyl group which is substituted with 1 to 2 groups selected from a lower alkoxy group and a lower alkanoyloxy group) can be also preferred by reducing a compound of the formula:

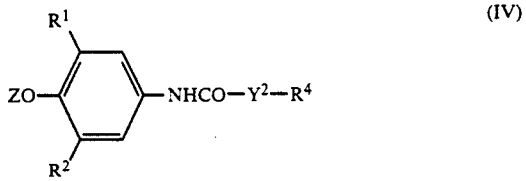

(wherein $Y^2$ represents a lower alkenylene group, and $R^1$, $R^2$, $R^4$ and ZO have the same meanings as defined above).

As the protective group of the hydroxyl group in the starting compounds (II) and (IV), any of those conventionally used can be used. For example, substituted or unsubstituted phenyl lower alkyl groups (e.g. benzyl group, p-methoxybenzyl group), substituted or unsubstituted phenyl lower alkoxycarbonyl groups (e.g. benzyloxycarbonyl group, p-methoxybenzyloxycarbonyl group), substituted or unsubstituted phenylsulfonyl groups (e.g. phenylsulfonyl group, p-methoxyphenylsulfonyl group), lower alkanoyl groups (e.g. acetyl group, propionyl group), etc. can be suitably used. As the salt of the compound (III) and the compounds (II) and (IV) wherein. ZO's are hydroxyl groups, alkali metal salts, alkaline earth metal salts and aluminum salts can be used, and as the salt of the compound (II) and the compounds (III) and (IV) containing pyrrolyl group which may be substituted with a lower alkyl group, inorganic acid addition salts and organic acid addition salts can be suitably used.

The condensation reaction between the aniline compound (II) or a salt thereof and the carboxylic acid compound (III) or its reactive derivative can be practiced in conventional manner. For example, when a reactive derivative of the carboxylic acid compound (III) is used, said condensation reaction can be practiced in an appropriate solvent in the presence or absence of a deacidifying agent. As the reactive derivative of the carboxylic acid compound (III), corresponding acid halides, mixed acid anhydrides and active esters can be preferably used, and as the deacidifying agent, for example, any of alkali metal hydroxides, alkali metal carbonates, alkali metal hydrogen carbonates, trialkylamine, N,N-dialkylaniline, pyridine and N-alkylmorpholine, etc. can be preferably used.

On the other hand, the condensation reaction between the aniline compound (II) or a salt thereof and the carboxylic acid compound (III) or a salt thereof can be practiced, for example, either in the presence or absence of a condensing agent. As the condensing agent, for example, any of condensing agents conventionally used such as N,N'-dicyclohexylcarbodiimide, N-cyclohexyl-N'-morpholinocarbodiimide and N-ethyl-N'-(3-dimethylaminopropyl)carbodiimide can be used.

The above-mentioned condensation reactions all proceed preferably in a solvent which does not affect the reaction such as dimethylformamide, tetrahydrofuran, dichloromethane, ethyl acetate, dimethyl sulfoxide, dioxane and acetonitrile, under ice-cooling to heating.

When ZO in the formula (II) is a protected hydroxyl group, subsequent removal of the protective group can be practiced suitably in conventional manner depending on the kind of said protective group.

Reduction reaction of the compound (IV) can be practiced in conventional manner. For example, the reduction reaction can be practiced by catalytic reduction in the presence of Raney nickel, Raney cobalt, palladium, platinum or rhodium catalyst, and can be also practiced in a lower alkanol by use of an alkali metal borohydride. In the latter case, if necessary, reduction may be also practiced in the presence of powdery tellurium, nickel chloride, cobalt chloride, copper chloride, palladium chloride, etc. Alternatively, the reduction reaction can be also practiced by use of an alkali metal or magnesium and a lower alkanol; zinc and an acid; lithium and ammonia or an amine; an activated nickel and water; or hydrazine and an oxidizing agent.

The free base or its salt of the desired product (I) of the present invention thus inhibits the 5-lipoxygenase, SRS-A (slow reacting substance of anaphylaxis: leukotriene $C_4/D_4/E_4$) and leukotriene $B_4$ formation, and PAF-induced death. Since SRS-A and leukotriene $B_4$ are thought to be mediators of various allergic and inflammatory reactions, the product (I) is expected to be useful for prophylaxis and treatment of various allergic and inflammatory diseases.

The desired product (I) of the present invention can be used either as such in the free form or in the form of its salt for pharmaceutical use, but particularly preferably in the free form.

The desired product (I) or its salt of the present invention can be administered either orally or parenterally. As the dosage form for parenteral administration, there may be included, for example, injection, ointment, aerosol, while as the dosage form for oral administration, tablet, capsule, granule, syrup, emulsion, suspension, etc.

The dose of the desired product (I) or its pharmacologically acceptable salt may depend on the administration route, the age, body weight, condition of the patient and the kind of the disease, but may be generally preferred to be within the range of 0.3 to 300 mg/kg/day.

Of the starting material compounds in the above reaction, the aniline compound (II) can be prepared by, for example, nitrating or nitrosating the 4-position of a phenol compound of the formula:

(wherein $R^1$, $R^2$ and ZO have the same meanings as defined above) in conventional manner, and further reducing the product.

EXPERIMENTAL EXAMPLE 1

5-Lipoxygenase inhibitory activity

An enzyme solution containing 5-lipoxygenase was prepared from cultured basophilic leukemia cell strain RBL-1 cells, and the reaction was carried out with radiolabelled arachidonic acid as the substrate in the presence of indomethacin, calcium chloride, adenosine triphosphate and the substance to be tested. A predetermined amount of the reaction mixture was spotted on a thin layer, separated by development, and then the radioactivity of the 5-HETE (5-hydroxyeicosatetraenic acid) fraction of the enzyme reaction product was measured to give the index of the 5-lipoxygenase activity.

The 5-lipoxygenase inhibitory activity of the substance tested is represented in terms of the concentration $IC_{50}$ ($\mu M$) which inhibits 50% of the reaction in the control test. [Method of M. Furukawa et al. described in Biochimica et Biophysica acta, vol. 795, p. 458 (1984)]

The experimental results are as shown below in Table 1.

TABLE 1

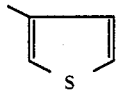

| $R^1$ and $R^2$ | Y | $R^3$ | 5-Lipoxygenase inhibitory activity $IC_{50}$ ($\mu M$) |
|---|---|---|---|
| both —CH$_3$ | Single bonding arm | 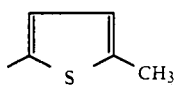 | 0.81 |
|  |  | 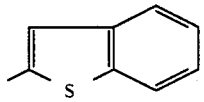 | 0.27 |
|  |  |  | 0.21 |
|  | 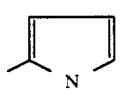 | 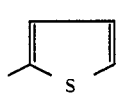 | 0.20 |
|  |  | 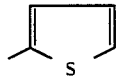 | 0.44 |
|  | —(CH$_2$)$_2$— | 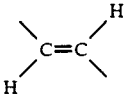 | 0.76 |
| both —CH(CH$_3$)$_2$ | Single bonding arm | 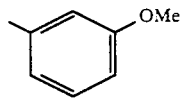 | 0.15 |
| both —CH$_3$ | 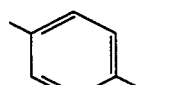 | 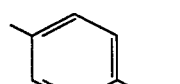 | 0.24 |
|  |  | 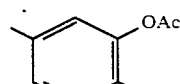 | 0.22 |
|  |  |  | 0.15 |
|  | —(CH$_2$)$_2$— |  | 0.20 |

TABLE 1-continued $$\text{HO}-\underset{\underset{R^2}{|}}{\overset{\overset{R^1}{|}}{C_6H_2}}-\text{NHCO}-Y-R^3$$

| R¹ and R² | Y | R³ | 5-Lipoxygenase inhibitory activity IC$_{50}$ (μM) |
|---|---|---|---|
| | | 4-MeO-C$_6$H$_4$— | 0.25 |
| both —CH(CH$_3$)$_2$ | $\text{H}_3\text{C}\diagdown\text{C}=\text{C}\diagup\text{H}$ (with H on other side) | | 0.15 |
| both —CH$_3$ | | —(CH$_2$)$_5$CH$_3$ | 0.30 |
| | | —(CH$_2$)$_6$CH$_3$ | 0.33 |
| | | —(CH$_2$)$_7$CH$_3$ | 0.40 |
| | | —(CH=CH)$_2$CH$_3$ | 0.40 |

(In Table, Me represents methyl group and Ac represents acetyl group, hereinafter the same)

EXPERIMENTAL EXAMPLE 2

Leukotriene C$_4$ formation inhibitory activity

Lung fragments of guinea pig sensitized with ovalbumin were treated with the test compound and challenged with ovalbumin in vitro. After solvent extraction, leukotriene C$_4$ in the supernatant was determined by radioimmunoassay. The leukotriene C$_4$ formation inhibitory activity of the test compound is expressed as % inhibition at the sample concentration of $10^{-5}$ M.

The experimental results are as shown below in Table 2.

TABLE 2

$$\text{HO}-\underset{\underset{R^2}{|}}{\overset{\overset{R^1}{|}}{C_6H_2}}-\text{NHCO}-Y-R^3$$

| R¹ and R² | Y | R³ | Leukotriene C$_4$ formation inhibitory activity (%) |
|---|---|---|---|
| both —CH$_3$ | Single bonding arm | 2-thienyl | 62.9 |
| | | 2-methylthienyl | 76.6 |
| | | 2,5-dimethylthienyl (—CH$_3$) | 59.0 |
| | —(CH$_2$)$_2$— | 2-methylthienyl | 45.8 |
| | $\diagdown\text{C}=\text{C}\diagup$ (trans —CH=CH—) | 2-methylthienyl | 65.0 |

TABLE 2-continued

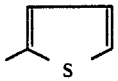

| $R^1$ and $R^2$ | Y | $R^3$ | Leukotriene $C_4$ formation inhibitory activity (%) |
|---|---|---|---|
| both —CH(CH$_3$)$_2$ | Single bonding arm | 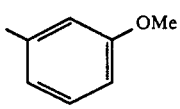 | 79.9 |
| both —CH$_3$ | —(CH$_2$)$_2$— | 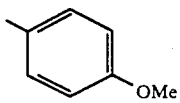 (OMe, meta) | 66.9 |
|  |  | 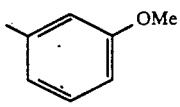 (OMe, para) | 49.3 |
|  | 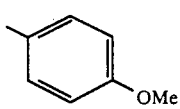 (CH=CH, H/H) | 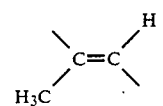 (OMe, meta) | 46.0 |
|  | 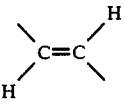 (CH=C, H$_3$C/H) | 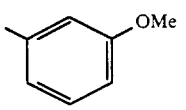 (OMe, para) | 58.1 |
|  | —CHCH$_2$—<br>    \|<br>   CH$_3$ |  | 58.9 |
| both —C(CH$_3$)$_3$ | 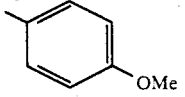 (CH=C, H$_3$C/H) |  | 58.3 |

EXPERIMENTAL EXAMPLE 3

Leukotriene $B_4$ formation inhibitory activity

A neutrophil suspension, prepared by administration of casein intraperitoneally to guinea pig, was treated with the test compound and challenged with calcium ionophore A23187 and arachidonic acid. After solvent extraction, leukotriene $B_4$ was assayed by high performance liquid chromatography. The leukotriene $B_4$ formation inhibitory activity of the test compound is expressed as % inhibition at the sample concentration of $10^{-6}$ M. [Method of Douglass et al. described in Prostaglandins vol. 31, p. 358 (1986)]

The experimental results are as shown below in Table 3.

TABLE 3

| $R^1$ and $R^2$ | Y | $R^3$ | Leukotriene $B_4$ formation inhibitory activity (%) |
|---|---|---|---|
| both —CH$_3$ | C=C (H/H) | OMe (meta) | 62.6 |
|  |  | OMe (para) | 65.6 |

TABLE 3-continued $$\text{HO}-\underset{R^2}{\underset{|}{\overset{R^1}{\overset{|}{\bigcirc}}}}-\text{NHCO}-Y-R^3$$

| R¹ and R² | Y | R³ | Leukotriene B₄ formation inhibitory activity (%) |
|---|---|---|---|
| | | (phenyl with OAc, OAc) | 82.0 |
| | —(CH₂)₂— | (phenyl with OAc, OAc) | 81.9 |
| both —CH(CH₃)₂ | (CH₃)C=CH (trans) | (phenyl-OMe) | 88.8 |
| both —CH₃ | | —(CH₂)₅CH₃ | 53.1 |
| | | —(CH₂)₆CH₃ | 59.7 |
| | | —(CH₂)₇CH₃ | 57.3 |
| both —CH₃ | | geranyl (E) | 82.5 |
| | | geranyl (Z) | 95.3 |
| | | farnesyl (all-E) | 90.5 |
| | | farnesyl (Z,Z,E) | 98.5 |
| both —C₂H₅ | | —(CH₂)₆CH₃ | 85.6 |
| both —CH(CH₃)₂ | | | 69.5 |

EXPERIMENTAL EXAMPLE 4

PAF induced death protective effect

The test compound was administered intraperitoneally into the mouse, and 30 minutes later, PAF (100 μg/kg) was administered through the tail vein, and the survival rate one hour after PAF administration was determined.

The compounds shown in Table 4 exhibited the survival rate of 100% by administration of 30 mg/Kg.

TABLE 4

$$\text{HO}-\underset{R^2}{\underset{|}{\overset{R^1}{\overset{|}{\bigcirc}}}}-\text{NHCO}-Y-R^3$$

| R¹ and R² | Y | R³ |
|---|---|---|
| both —CH₃ | Single bonding arm | (thienyl) |

TABLE 4-continued

![structure: HO-phenyl(R1,R2)-NHCO-Y-R3]

| R¹ and R² | Y | R³ |
|---|---|---|
| | | (2-thienyl) |
| | | (5-methyl-2-thienyl) |
| | | (indol-2-yl, NH) |
| | | (benzothiophen-2-yl) |
| both —C₂H₅<br>both —CH(CH₃)₂ | Single bonding arm | (1-methylpyrrol-2-yl) |
| both —CH₃ | —(CH₂)₂— | (2-thienyl) |
| | | (4-methoxyphenyl) |
| both —CH(CH₃)₂ | —(CH₂)₆CH₃ | (CH₃-CH=C(CH₃)-CH₂-CH₂-CH=C(CH₃)- group) |

EXAMPLE 1

Under ice-cooling, 128 mg of 2-thienylcarboxylic acid is dissolved in 3 ml of acetonitrile, and to the resultant solution are added 303 mg of triethylamine, then 207 mg of diethylphosphorochloridate. After the mixture is stirred for 30 minutes, 201 mg of 4-amino-2,6-diethylphenol is added and the reaction mixture is stirred at room temperature. After completion of the reaction, ice chips are added, and then an aqueous 5 % sodium hydrogen carbonate is added. The crystals precipitated are collected by filtration, washed with isopropyl ether and the residue is recrystallized from ethyl acetate to give 150 mg of 4-(2-thienylcarbonyl)amino-2,6-diethylphenol as white crystals.

M.p. 190 to 191.5° C.,
Mass (m/e): 275, 111, Nujol.
IR $\nu_{max}$ (cm⁻¹): 3480, 3300, 1630
NMR (DMSO-d₆) δ: 1.15 (t, 7.3Hz, 6H), 2.59 (q, 7.3Hz, 4H), 7.18 (dd, 3.7 and 5Hz, 1H), 7.28 (s, 2H), 7.77 (dd, 1.1 and 5.0Hz, 1H), 7.96 (dd, 1.1 and 3.7Hz, 1H).

EXAMPLE 2

Under ice-cooling, 4.16 g of 2,5-dimethoxycinnamic acid is dissolved in 50 ml of acetonitrile, and to the resultant solution are added 3.03 g of triethylamine, then 4.13 g of diethylphosphorochloridate. After the mixture is stirred for one hour, 2.74 g of 4-amino-2,6-dimethylphenol is added and the reaction mixture is stirred at room temperature. After completion of the reaction, ice chips are added, and then 5 % aqueous sodium hydrogen carbonate solution is added. The crystals precipitated are collected by filtration, and washed with isopropyl ether. The crystals obtained are recrystallized form ethyl acetate to give 4.64 g of 4-(2,5-dimethoxycinnamoylamino)-2,6-dimethylphenol as white crystals.

5 M.p. 198.5° to 199.5° C. (decomposed),
Mass (m/e): 327, 191, 176, 137 Nujol.
IR $\nu_{max}$ (cm⁻): 3400, 3330. 1645.
NMR (DMSO-d₆) δ; 2.16 (s, 6H), 3.76 (s, 3H), 3.82 (s, 3H), 6.81 (d, 15.8Hz, 1H), 6.93 to 7.08 (m, 3H), 7.25 (s, 2H), 7.72 (d, 15.8Hz, 1H).

EXAMPLE 3

Under ice-cooling, to a solution of 0.9 g of 3,7,11-trimethyl-(2Z,6E)-2,6,10-dodecatrienoic acid in 10 m of acetonitrile are added 578 mg of triethylamine, then 854 mg of diethylphosphorochloridate. After the mixture is stirred for 30 minutes, 522 mg of 4-amino-2,6-dimethylphenol is added and the reaction mixture is stirred at room temperature. Ice chips are added into the reaction mixture, the mixture is extracted with isopropyl ether and the extracted with 10% hydrochloric acid, water, 5% aqueous sodium hydrogen carbonate and saturated aqueous sodium chloride, followed by drying and then evaporation of the solvent. The residue is purified by silica gel column chromatography [solvent: ethyl acetate-hexane (1:3)] to give 580 mg of 4-[3,7,11-trimethyl-(2Z,6E)-2,6,10-dodecatrienoylamino]-2,6-dimethylphenol.

Mass (m/e): 335 (M⁺), 286, 219, 137, Liquid,
IR $\nu_{max}$ (cm⁻¹): 3310, 1660.
NMR (CDCl₃) δ: 1.59 (s, 3H), 1.61 (s, 3H), 1.67 (s, 3H), 1.87 (d, 1.5Hz, 3H), 2.04 (m, 4H), 2.19 (s, 6H), 2.26 (t, 8Hz, 2H), 2.70 (t, 8Hz, 2H), 5.0 to 5.2 (m, 2H), 5.65 (d, 1.5Hz, 1H), 7.07 (s, 2H).

EXAMPLE 4

Under ice-cooling and N₂ atmosphere, a solution of 1.47 g of 2-thiophenecarbonyl chloride in 10 ml of methylene chloride is added to a mixture of 2.91 g of 4-amino-2,6-diisopropylphenol hydrochloride, 90 ml of ethyl acetate, 80 ml of water, and 8.0 g of sodium hydrogen carbonate during a period of 30 minutes. After stirring at room temperature for one hour, organic layer is separated, washed with water, 10 % HCl, water, dried, and concentrated. The obtained solid is recrystallized from chloroform-hexane to give 1.7 g of 4-(2-thienylcarbonyl)-amino-2,6-diisopropylphenol.

M.p. 198° to 199° C.,
Mass (m/e): 303, 288, 111, Nujol,
IR $\nu_{max}$ (cm⁻¹): 3600, 3260, 1630.

NMR (DMSO d$_6$) δ: 1.17 (d, 6.8Hz, 12H), 3.30 (heptet, 6.6Hz, 2H), 7.19 (dd, 4 and 5Hz, 1H), 7.36 (s, 2H), 7.78 (dd, 0.9 and 5Hz, 1H), 7.97 (dd, 0.9 and 4Hz, 1H).

EXAMPLE 5

Under argon gas stream, to a solution of 600 mg of 4-amino-2,6-dimethylphenol in 20 ml of tetrahydrofuran is added under ice-cooling 779 mg of 3-methoxycinnamic acid, and then 902 mg of dicyclohexylcarbodiimide and 118 mg of 1-hydroxybenzotriazole are added, followed by stirring at room temperature overnight. After ethyl acetate is added to the reaction mixture, the mixture is washed successively with 10 % hydrochloric acid, water, 5 % sodium hydrogen carbonate and water, and dried, followed by concentration. The residue is recrystallized from ethyl acetate-n-hexane to give 890 mg of 4-(3-methoxycinnamoyl)amino-2,6-dimethylphenol.

M.p. 195.5° to 197° C.
Mass (m/e): 297, 161, 137, Nujol.
IR $\nu_{max}$ (cm$^{-1}$): 3320, 3230, 1650,
NMR (DMSO-d$_6$) δ: 2.15 (s, 6H), 3.80 (s, 3H), 6.77 (d, 15Hz, 1H), 7.24 (s, 2H), 7.49 (d, 15Hz, 1H).

EXAMPLE 6

(1) To a solution of 1.6 g of 4-benzyloxy-3,5-dimethylaniline in 30 ml of dimethylformamide is added under ice-cooling 1.17 g of potassium carbonate, and then a solution of 2.0 g of 3,4-diacetoxycinnamoyl chloride in 10 ml of dimethylformamide is added dropwise at 5° to 7° C., followed by stirring at room temperature for 2 hours. The reaction mixture is poured into ice-water, adjusted to pH 1 with 10 % hydrochloric acid and extracted with ethyl acetate. The extract is washed with water, dried and then concentrated. Recrytallization of the residue from methanol gives 2.64 g of N-(3,4-diacetoxycinnamoyl)-4-benzyloxy-3,5-dimethylaniline.

M.p. 125° to 127° C.
Mass (m/e): 473, 382, chloroform.
IR $\nu_{max}$ (cm$^{-1}$): 3430, 1770, 1680.
NMR (CDCl$_3$) δ: 2.29 (s, 12H), 4.79 (s, 2H), 6.41 (d, 16Hz, 1H), 7.25 (s, 5H), 7.35 (s, 2H), 7.32 to 7.50 (m, 3H).

(2) One hundred (100) mg of the product of the above (1) is catalytically reduced in a mixture of 5 ml of ethanol and 5 ml of tetrahydrofuran at room temperature under ordinary pressure in the presence of 30 mg of 10 % palladium-carbon. After completion of the reaction, palladium-carbon is filtered off, and the reaction mixture is washed with tetrahydrofuran. The filtrate and the washing are concentrated under reduced pressure, and the residue is recrystallized from isopropyl ether-n-hexane to give 58 mg of 4-[3-(3,4-diacetoxyphenyl)propionyl]amino-2,6-dimethylphenol.

M.p. 118° to 119° C.,
Mass (m/e): 385,
NMR (CDCl$_3$) δ: 2.19 (s, 6H) 2.27 (s, 6H), 2.56 (t, 7Hz, 2H), 3.03 (t, 7Hz, 2H), 7.08 (s, 2H).

EXAMPLE 7

(1) 1.0 g of 4-benzyloxy-3,5-dimethylaniline and 30 ml of nonanoic acid are stirred at 150° C. for 3 hours. To the reaction mixture is added 100 ml of ether, and the mixture is washed with an aqueous 10 % sodium hydroxide and water, and dried followed by evaporation of the solvent. The residue is purified by silica gel column chromatography [Solvent:chloroform-ethanol (10:1)], and from the eluate is obtained 260 mg of N-(4-benzyloxy-3,5-dimethylphenyl)nonaneamide as an oily product.

(2) 1.2 g of the product of the above (1) is catalytically reduced in 20 ml of ethanol and 10 ml of tetrahydrofuran at room temperature under ordinary pressure in the presence of 300 mg of 10 % palladium-carbon. The palladium-carbon is filtered off from the reaction mixture, and the solvent is evaporated from the filtrate. Recrystallization of the residue from isopropyl ether gives 900 mg of 4-nonanoylamino-2,6-dimethylphenol.

M.p. 100.5° to 101° C. (isopropyl ether).
NMR (CDCl$_3$) δ: 0.87 (t, 7Hz, 3H), 1.28 (bs, 10H), 1.52 to 1.79 (m, 2H), 2.21 (s, 6H), 4.57 (s, 1H), 6.92 (broad, 1H), 7.09 (s, 2H).

EXAMPLES 8 to 38

The corresponding starting compounds were treated similarly as in either one of Examples 1 to 7 to obtain the compounds shown below in Tables 5 to 13.

TABLE 5

HO—[2,6-dimethylphenyl]—NHCO—Y—R$^3$ (provided that Y is single bonding arm)

| Example No. | R$^3$ | Physical properties |
|---|---|---|
| 8 | 2,3-dihydrofuran-2-yl (S-containing, thiolane) | M.p. 178.5 to 180.0° C. (methanol-chloroform) IR $\nu_{max}^{Nujol}$ (cm$^{-1}$): 3400, 3220, 1620 |
| 9 | thiophen-2-yl | M.p. 183 to 183.5° C. (methanol-chloroform) IR $\nu_{max}^{Nujol}$ (cm$^{-1}$): 3400, 3240, 1620 |
| 10 | benzothiophen-2-yl | M.p. 205.5 to 206° C. (methanol-chloroform) IR $\nu_{max}^{Nujol}$ (cm$^{-1}$): 3380, 1635 |
| 11 | indol-2-yl | M.p. 244 to 247° C. (ethyl acetate-isopropyl ether-hexane) IR $\nu_{max}^{Nujol}$ (cm$^{-1}$): 3400, 3260, 1620 |
| 12 | indol-3-yl | M.p. 182.5° C. (decomposed) (ethyl acetate-isopropyl ether-hexane) IR $\nu_{max}^{Nujol}$ (cm$^{-1}$): 3400, 3255, 1610 |
| 13 | 5-methylthiophen-2-yl | M.p. 155.5 to 157.5° C. (chloroform) IR $\nu_{max}^{Nujol}$ (cm$^{-1}$): 3420, 3260, 1605 |

TABLE 6

$R^1$, $R^2$ on HO-phenyl-NHCO—Y—$R^3$ (provided that Y is single bonding arm)

| Example No. | $R^1$ and $R^2$ | Y—$R^3$ | Physical properties |
|---|---|---|---|
| 14 | both —C(CH$_3$)$_3$ | 2-thienyl | M.p. 245° C. (decomposed) (chloroform) IR $\nu_{max}^{Nujol}$ (cm$^{-1}$): 3640, 3300, 1620 |

TABLE 7

3,5-dimethyl-4-hydroxyphenyl-NHCO—Y—$R^3$ (provided that Y represents trans-vinylene group in Examples 15 to 17)

| Example No. | $R^3$ | Physical properties |
|---|---|---|
| 15 | 2-thienyl | M.p. 213 to 215° C. (methanol-chloroform) IR $\nu_{max}^{Nujol}$ (cm$^{-1}$): 3440, 3250, 1650 |
| 16 | N-methyl-2-pyrrolyl | M.p. 263 to 265.5° C. (methanol) IR $\nu_{max}^{Nujol}$ (cm$^{-1}$): 3390, 3250, 1650 |
| 17 | 2-indolyl (NH) | M.p. 223 to 225° C. (methanol-chloroform) IR $\nu_{max}^{Nujol}$ (cm$^{-1}$): 3400, 3300 (broad) 1650 |

TABLE 8

3,5-dimethyl-4-hydroxyphenyl-NHCO—Y—$R^3$

| Example No. | Y | $R^3$ | Physical properties |
|---|---|---|---|
| 18 | trans-CH=CH— | 4-MeO-phenyl | M.p. 165 to 167° C. (chloroform) IR $\nu_{max}^{Nujol}$ (cm$^{-1}$): 3300, 3260 1660 |
| 19 | trans-CH=CH— | 3,4-(MeO)$_2$-phenyl | M.p. 194 to 196° C. IR $\nu_{max}^{Nujol}$ (cm$^{-1}$): 3500, 3280 1650 |
| 20 | trans-CH=CH— | 3,4-(OAc)$_2$-phenyl | M.p. 194.5 to 196.5° C. (ethanol-n-hexane) IR $\nu_{max}^{Nujol}$ (cm$^{-1}$): 3360, 1760 1655 |

(In the table, Ph represents a phenyl group, hereinafter the same)

TABLE 9

$R^1$, $R^2$ on HO-phenyl-NHCO—C(CH$_3$)=CH—$R^3$

| Example No. | $R^1$ and $R^2$ | $R^3$ | Physical properties |
|---|---|---|---|
| 21 | both —CH$_3$ | 4-MeO-phenyl | M.p. 158 to 160° C. (ethyl acetate) IR $\nu_{max}^{Nujol}$ (cm$^{-1}$): 3330, 3260, 1620 |
| 22 | both —CH(CH$_3$)$_2$ | 4-MeO-phenyl | M.p. 148 to 150° C. (isopropyl ether-chloroform) IR $\nu_{max}^{Nujol}$ (cm$^{-1}$): 3460, 3370, 1650 |
| 23 | both —C(CH$_3$)$_3$ | 4-MeO-phenyl | M.p. 198.5 to 199.5° C. (isopropyl ether-chloroform) IR $\nu_{max}^{Nujol}$ (cm$^{-1}$): 3610, 3260, 1640 |

TABLE 10

3,5-dimethyl-4-hydroxyphenyl-NHCO—Y—$R^3$

| Example No. | Y | $R^3$ | Physical properties |
|---|---|---|---|
| 24 | —(CH$_2$)$_3$— | 3-MeO-phenyl | M.p. 134 to 135° C. (ethyl acetate) IR $\nu_{max}^{Nujol}$ (cm$^{-1}$): 3405, 3280 1650 |
| 25 | —CH(CH$_3$)— | 4-MeO-phenyl | M.p. 147 to 148.5° C. (chloroform-isopropyl ether) IR $\nu_{max}^{Nujol}$ (cm$^{-1}$): 3340, 3270 1645 |
| 26 | —CH(CH$_3$)— | 3,4-(MeO)$_2$-phenyl | M.p. 200 to 201.5° C. (methanol) IR $\nu_{max}^{Nujol}$ (cm$^{-1}$): 3500, 3310 1660 |
| 27 | —CH(Me)CH$_2$— | 4-MeO-phenyl | M.p. 132 to 133° C. (methanol-isopropyl ether) IR $\nu_{max}^{Nujol}$ (cm$^{-1}$): 3430, 3280 1625 |

TABLE 11

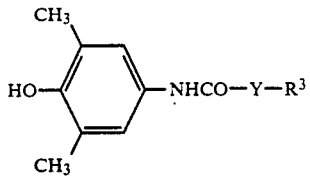

| Example No. | Y—R³ | Physical properties |
|---|---|---|
| 28 | ⟋⟍⟋⟍CH₃ | M.p. 180 to 182.5° C. (isopropyl alcohol-isopropyl ether) IR $\nu_{max}^{Nujol}$ (cm⁻¹): 3420, 3280 1660 |
| 29 | —(CH₂)₅—CH₃ | M.p. 91.5 to 93° C. (isopropyl ether) IR $\nu_{max}^{Nujol}$ (cm⁻¹): 3420, 3275 1645 |
| 30 | —(CH₂)₈—CH₃ | M.p. 101 to 103° C. (isopropyl ether) IR $\nu_{max}^{Nujol}$ (cm⁻¹): 3430, 3280 1650 |
| 31 | (branched chain with CH₃, CH₃, CH₃) | M.p. 91 to 93° C. (isopropyl ether-hexane) IR $\nu_{max}^{Nujol}$ (cm⁻¹): 3240, 1655 1630 |
| 32 | (branched chain with CH₃, CH₃, CH₃) | M.p. 103 to 105° C. (isopropyl ether-hexane) IR $\nu_{max}^{Nujol}$ (cm⁻¹): 3430, 3260 1655, 1620 |
| 33 | (branched chain with CH₃, CH₃, CH₃, CH₃) | (Oily product) IR $\nu_{max}^{Liquid}$ (cm⁻¹): 3300, 1660, 1630 |

TABLE 12

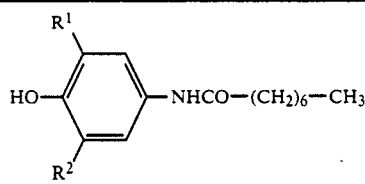

| Example No. | R¹ and R² | Physical properties |
|---|---|---|
| 34 | both —C₂H₅ | M.p. 93.5 to 95.5° C. (isopropyl ether) IR $\nu_{max}^{Nujol}$ (cm⁻¹): 3430, 3260 1650 |
| 35 | both —CH(CH₃)₂ | (Oily product) IR $\nu_{max}^{Liquid}$ (cm⁻¹): 3300, 1650 |
| 36 | both —C(CH₃)₃ | M.p. 98.5 to 100° C. (hexane) IR $\nu_{max}^{Nujol}$ (cm⁻¹): 3620, 3290 1645 |

TABLE 13

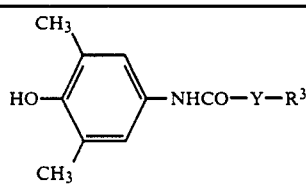

| Example No. | Y—R³ | Physical properties |
|---|---|---|
| 37 | —(CH₂)₆—CH₃ | M.p. 103 to 104.5° C. (isopropyl ether) IR $\nu_{max}^{Nujol}$ (cm⁻¹): 1680 |

TABLE 13-continued

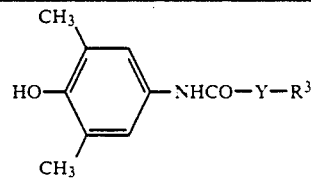

| Example No. | Y—R³ | Physical properties |
|---|---|---|
| 38 | (branched chain with CH₃, CH₃, CH₃) | M.p. 134.5 to 136° C. (isopropyl ether-hexane) IR $\nu_{max}^{Nujol}$ (cm⁻¹): 3300, 3240 1650 |

EXAMPLE 39

A mixture of 2.5 g of trans-4-[3-(2-thenyl)acryloyl]-amino-2,6-dimethylphenol, 2.38 g of sodium borohydride, 2.9 g of powdery tellurium is refluxed under stirring in 100 ml of ethanol for 1.5 hours. After cooling, the insolubles are filtered off, and the filtrate is concentrated. The residue is dissolved in 20 ml of acetic acid and diluted with water. The precipitated crystals are recovered by filtration to give 1.78 g of 4-[3-(2-thienyl)-propionyl]amino-2,6-dimethylphenol.

M.p. 157.5°–159° C. (acetic acid-water), Nujol,
IR $\nu_{max}$ (cm⁻¹): 3420, 3250, 1630.

EXAMPLE 40

The corresponding starting material compounds were treated similarly as in Example 39 to obtain the compounds shown below in Table 14.

TABLE 14

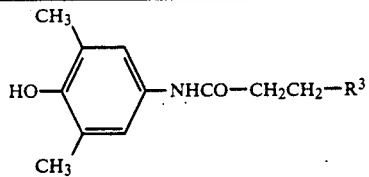

| Example No. | $R^3$ | Physical properties |
|---|---|---|
| 40 | 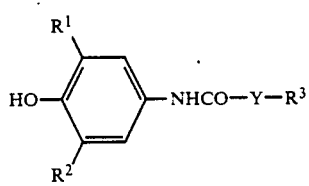 | M.p. 149.5 to 150° C. (chloroform-isopropyl ether) IR $\nu_{max}^{Nujol}$ (cm$^{-1}$): 3330, 3260, 1620 |

We claim:

1. A 4-aminophenol derivative of the formula:

HO—⟨phenyl with $R^1$, $R^2$⟩—NHCO—Y—$R^3$ (wherein $R^1$ and $R^2$ each represent a lower alkyl group, Y represents a single bonding arm, a lower alkylene group or a lower alkenylene group, $R^3$ represents a thienyl group or pyrrolyl group which may be also substituted with a lower alkyl group; benzothienyl group, indolyl group; or a phenyl group which is substituted with 1 to 2 groups selected from a lower alkoxy group and a lower alkanoyloxy group; or Y-$R^3$ represents integrally an alkyl group with 6 to 9 carbon atoms; or a hydrocarbon group with 5 to 14 carbon atoms having 2 or 3 double bonds) or a pharmacologically acceptable salt thereof.

2. A compound according to claim 1, wherein Y is a single bonding arm, a lower alkylene group or a lower alkenylene group, and $R^3$ is a thienyl group or pyrrolyl group which may be also substituted with a lower alkyl group, a benzothienyl group or an indolyl group.

3. A compound according to claim 1, wherein Y is a single bonding arm, a lower alkylene group or a lower alkenylene group, and $R^3$ is a phenyl group substituted with 1 to 2 groups selected from a lower alkoxy group and a lower alkanoyloxy group.

4. A compound according to claim 1, wherein Y-$R^3$ represents integrally an alkyl group with 6 to 9 carbon atoms or a hydrocarbon group with 5 to 14 carbon atoms having 2 or 3 double bonds.

5. A compound according to claim 1, wherein $R^1$ and $R^2$ each represent an alkyl group with 1 to 4 carbon atoms, Y represents a single bonding arm, an alkylene group with 1 to 4 carbon atoms or an alkenylene group with 2 to 4 carbon atoms, $R^3$ represents thienyl group, a 2-($C_{1-4}$-alkyl)thienyl group, pyrrolyl group, N-($C_{1-4}$-alkyl)pyrrolyl group, benzothienyl group, indolyl group, a 3- or 4-($C_{1-4}$-alkoxy)phenyl group, a 3,4-di($C_{1-4}$-alkoxy)phenyl group, a 2,5-di($C_{1-4}$-alkoxy)phenyl group or a 3,4-di($C_{2-5}$-alkanoyloxy)phenyl group, or Y-$R^3$ integrally represents an alkyl group with 6 to 9 carbon atoms or a hydrocarbon group with 5 to 14 carbon atoms having 2 or 3 double bonds.

6. A compound according to claim 5, wherein Y is a single bonding arm, an alkylene group with 1 to 4 carbon atoms or an alkenylene group with 2 to 4 carbon atoms, $R^3$ is thienyl group, a 2-($C_{1-4}$-alkyl)thienyl group, pyrrolyl group, a N-($C_{1-4}$-alkyl)pyrrolyl group, benzothienyl group or indolyl group.

7. A compound according to claim 5, wherein Y is a single bonding arm, an alkylene group with 1 to 4 carbon atoms or an alkenylene group with 2 to 4 carbon atoms, $R^3$ is a 3- or 4-($C_{1-4}$-alkoxy)phenyl group, a 3,4-di($C_{1-4}$-alkoxy)phenyl group, a 2,5-di($C_{1-4}$-alkoxy)phenyl group or a 3,4-di($C_{2-5}$-alkanoyloxy)phenyl group.

8. A compound according to claim 5, wherein Y-$R^3$ represents integrally an alkyl group with 6 to 9 carbon atoms or a hydrocarbon group with 5 to 14 carbon atoms having 2 or 3 double bonds 9. 4-(3-Thienyl)carbonylamino-2,6-dimethylphenol or a pharmacologically acceptable salt thereof.

10. 4-(3,7-Dimethyloctane-2,6-dienoylamio)-2,6-dimethylphenol or a pharmacologically acceptable salt thereof.

11. 4-Octanoylamino-2,6-diethylphenol or a pharmacologically acceptable salt thereof.

* * * * *